United States Patent [19]
Bolbolan

[11] Patent Number: 5,931,673
[45] Date of Patent: Aug. 3, 1999

[54] INTRAORAL DENTAL DAM

[76] Inventor: Mitra Bolbolan, 143A S. Camden Dr., Beverly Hills, Calif. 90212

[21] Appl. No.: 09/055,150

[22] Filed: Apr. 4, 1998

[51] Int. Cl.$^6$ ................ A61C 5/14; A61C 5/12
[52] U.S. Cl. .......................... 433/136; 433/138
[58] Field of Search .................... 433/136, 138, 433/91, 93, 96

[56] References Cited

U.S. PATENT DOCUMENTS

| | | | |
|---|---|---|---|
| 2,937,445 | 5/1960 | Erickson | 433/93 |
| 3,396,468 | 8/1968 | Dayhoff | 433/93 |
| 3,772,790 | 11/1973 | Swan-Gett et al. | 433/136 |
| 4,828,491 | 5/1989 | Gray | 433/136 |
| 5,011,409 | 4/1991 | Gray | 433/136 |
| 5,516,286 | 5/1996 | Kushner | 433/93 |

Primary Examiner—Nicholas D. Lucchesi
Attorney, Agent, or Firm—Michael Zarrabian

[57] ABSTRACT

An intraoral dental dam including an elastic membrane attached to a resilient frame. The membrane having an upper, a lower, a middle portion corresponding to the oral cavity of the user, the middle portion extending between the upper and lower portions, and a perimeter. At least a portion of the perimeter of the membrane being attached to at least a portion of the frame to form an integral dental dam. The dental dam can be disposed in a user's mouth such that the upper portion rests against at least a portion of the palate, the lower portion rests over at least a portion of the tongue, the middle portion substantially blocks the oral cavity, and at least portions of the frame are proximate the inner portion of the user's upper and lower teeth, leaving said teeth substantially exposed.

20 Claims, 4 Drawing Sheets

5,931,673

INTRAORAL DENTAL DAM

FIELD OF THE INVENTION

The present invention relates to dental dams for use during dental procedures.

BACKGROUND

Dental dams are used during many dental procedures to prevent dental items or debris from entering a patient's oral cavity where they can be swallowed or inhaled, leading to potential injury. Further, dental dams are used where the dental materials require dry environments in and around a tooth to achieve their optimum physical properties. Referring to FIG. 1, an example conventional dental dam 10 includes a rubber membrane 15 which the dentist uses to isolate one tooth, or a series of teeth 20, by cutting out one or more small holes in the membrane 15 at locations corresponding to the teeth to be isolated. The dentist then places a portion of the membrane 15 in the patient's mouth with said teeth 20 protruding through corresponding holes in the membrane 15, thereby isolating said teeth. Clamps 25 are then used to hold the membrane 15 around the isolated teeth. Finally, the dentist stretches the periphery of the rubber membrane 15 over an extraoral frame 30, outside the mouth, to keep the membrane 15 held taut in front of the patient's face.

Existing dental dams have several disadvantages however. One disadvantage is that installing such dental dams requires the dentist to take several time consuming steps described above. When installed the dental dams are imposing, uncomfortable and the patients have to leave their mouths open during the entire dental procedure. Further, the dental dams are unstable and can easily collapse. For example, the rubber membrane can snap off the frame and the clamp can come off the tooth. This is specially problematic in Pedodontics where patients are typically young children who are impatient and frightened by the dental dams.

Another disadvantage of existing dental dams is that the patient must be anesthetized before the clamp can be used to hold the membrane around the isolated teeth. This is because the clamp exerts pressure to the tooth, causing severe pain. Administering anesthetics is time consuming and causes discomfort to the patient. Another disadvantage of a clamp, is that the pressure from the clamp can fracture a brittle tooth. This is common in Endodontics for root canal treatment where as part of the procedure, the teeth are made into hollow shells without any pulp therein. Further, the clamps are difficult and time consuming to fit and install around the teeth.

There is, therefore, a need for a dental dam which is simple to install, does not require an extraoral frame or clamps, and can be installed without anesthetizing the patient.

SUMMARY

The present invention satisfies these needs. In one embodiment, the present invention provides an intraoral dental dam comprising: (a) an elastic membrane having an upper portion, a lower portion, a middle portion corresponding to the oral cavity of the user, the middle portion extending between the upper and lower portions; and (b) a resilient frame, at least a portion of the perimeter of the membrane being attached to at least a portion of the frame to form an integral dental dam. The dental dam can be disposed in a user's mouth such that the upper portion rests against at least a portion of the palate, the lower portion rests over at least a portion of the tongue, the middle portion substantially blocks the oral cavity, and at least portions of the frame are proximate the inner portion of the user's upper and lower teeth, leaving said teeth substantially exposed.

Preferably, the frame comprises a closed loop spring-like member whereby the dental dam can be folded along the middle portion of the membrane and inserted into the mouth, such that a restoring action of the frame reopens the dental dam to a partially folded position and the upper portion of the dental dam rests against at least a portion of the palate, the lower portion rests over at least a portion of the tongue, the middle portion substantially blocks the oral cavity, and at least portions of the frame are proximate the inner portion of the user's upper and lower teeth, leaving said teeth substantially exposed. The frame can be selected such that the restoring action of the frame helps maintain the mouth in an open position. The frame can be shaped and sized to correspond substantially with the perimeter of the membrane.

The dental dam can further comprise a suction means along at least a portion of the frame for removing fluids from the mouth. The suction means comprises at least one suction tube having inlet openings along its walls for removing fluids from the mouth into the tube, and at least one outlet opening for removing fluids from the tube. Alternatively, at least a portion of the frame can comprise a tube having inlet openings along its walls for removing fluids from the mouth into the tube, and at least one outlet opening for removing fluids from the tube.

DRAWINGS

These and other features, aspects and advantages of the present invention will become better understood with regard to the following description, appended claims and accompanying drawings where:

DESCRIPTION

Figure 1:
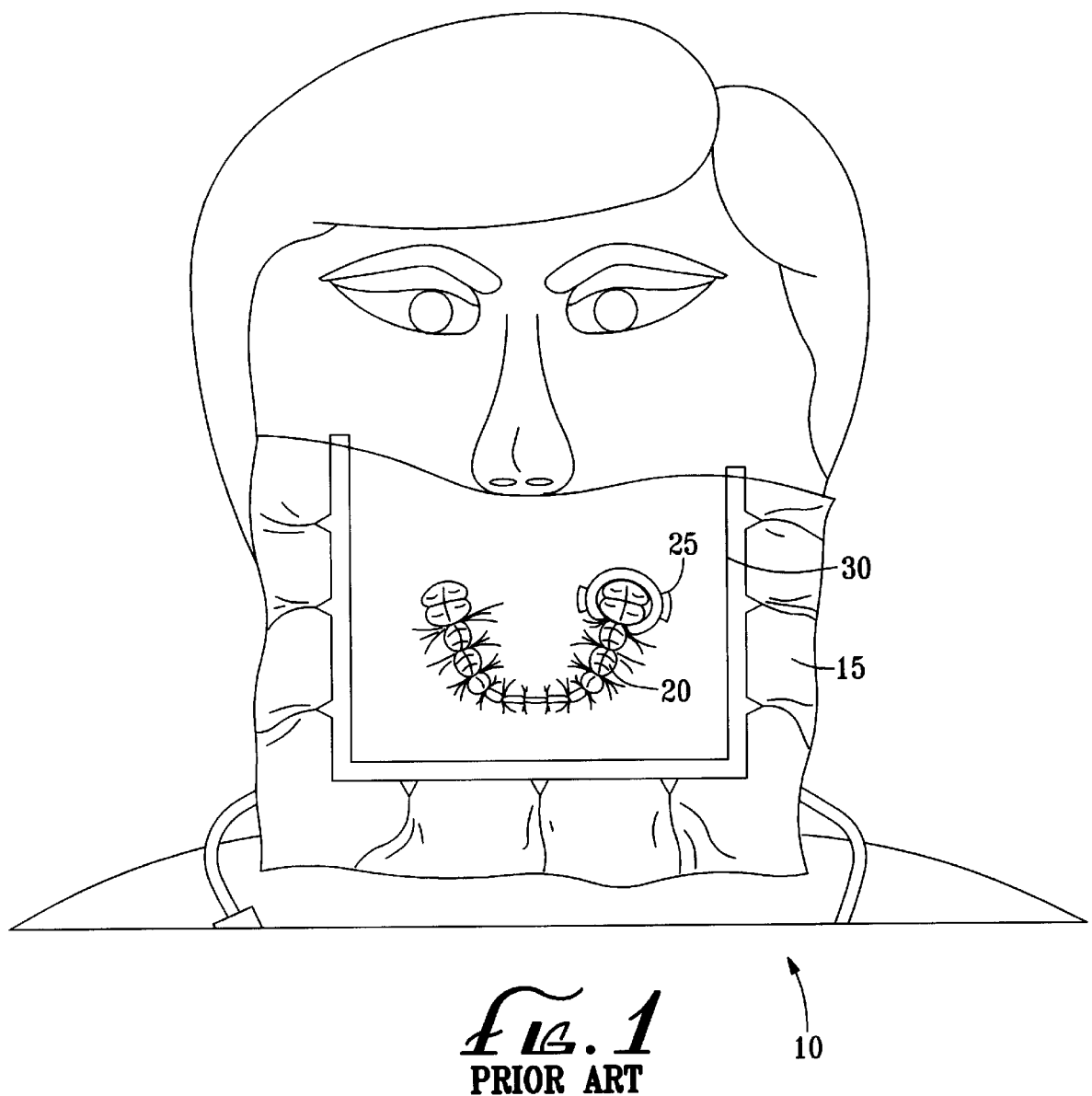
FIG. 1 is a front view of a prior art dental dam as installed in a patient's mouth.
Figure 2:
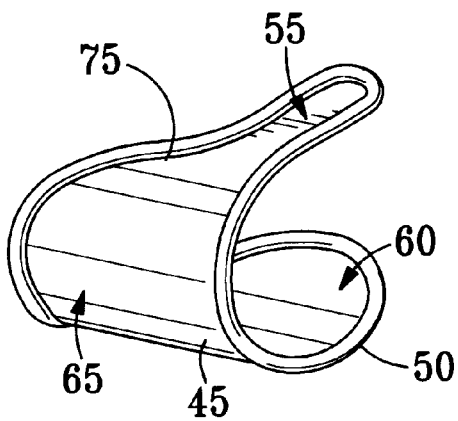
FIG. 2 is a perspective view of an embodiment of an intraoral dental dam according to the present invention in a semi-folded position.
Figure 3:
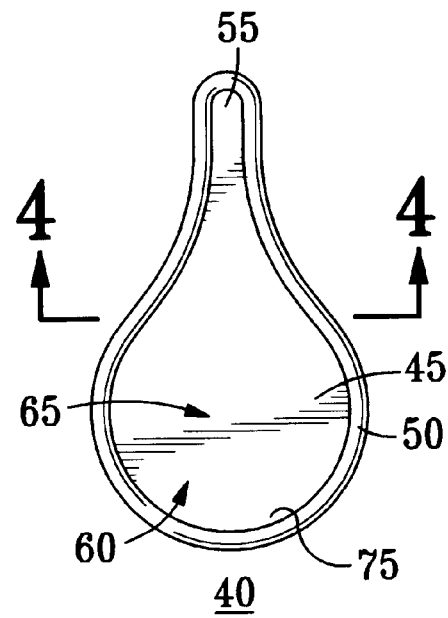
FIG. 3 is a plan view of the intraoral dental dam of FIG. 2.

Referring to FIGS. 2 and 3, an embodiment of an intraoral dental dam 40 according to the present invention comprises an elastic membrane 45 and a resilient frame 50, wherein the membrane 45 is attached to the frame 50. The membrane 45 includes an upper portion 55, a lower portion 60, a middle portion 65 corresponding to the oral cavity 70 in the user's mouth, the middle portion 65 extending between the upper and lower portions 55, 60; and a perimeter 75. At least a portion of the perimeter 75 of the membrane 45 is attached to at least a portion of the frame 40 to form an integral dental dam.

Figure 8:
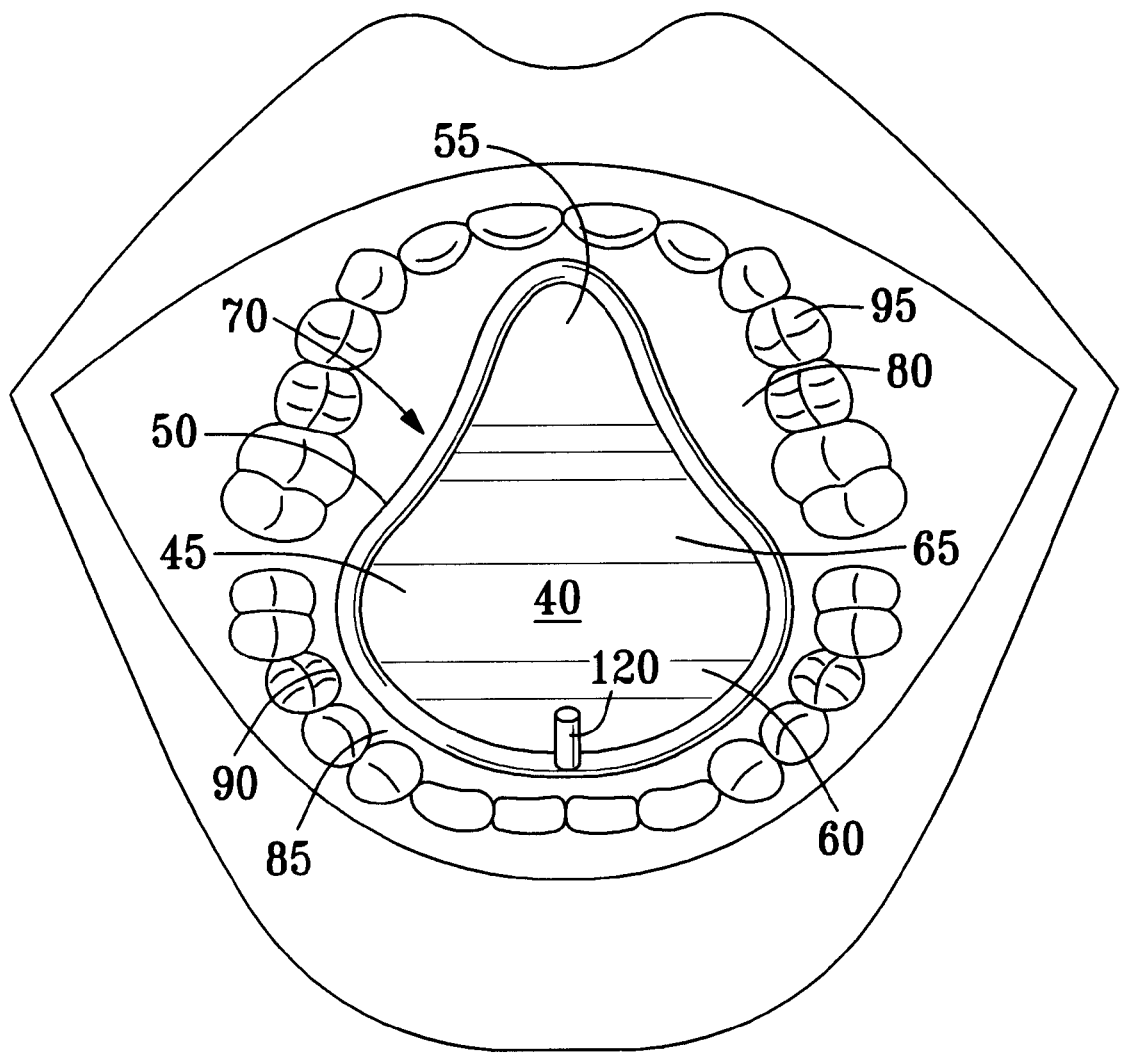
FIG. 8 shows an intraoral dental dam according to the present invention disposed in a patient's mouth.

As shown in FIG. 8, the dental dam 40 can be disposed in a user's mouth in a totally intraoral position such that, for example, the upper portion 55 rests against at least a portion of the palate 80, the lower portion 60 rests over at least a portion of the tongue 85, the middle portion 65 substantially blocks the oral cavity 70 at the end of the mouth of the user, and at least portions of the frame 50 are proximate the inner portion 90 of the user's teeth 95, leaving said teeth 95 substantially exposed. Whereby, the dental dam 40 substantially prevents objects such as debris from entering the user's oral cavity 70 by blocking such objects via the membrane 45.

The membrane 45 comprises an elastic sheet including materials such as rubber, plastic, silicone or combinations thereof. The membrane 45 can be porus such that only fluids can flow therethrough, or substantially non-porus. The membrane 45 is shaped and sized so that the dental dam 40 can fit within the mouth substantially adjacent the inner portion 90 of the teeth 95 and substantially block the oral cavity 70 as shown in FIG. 8. As such, the membrane 45 can be shaped and sized to fit various mouth sizes from young children to adults in an intraoral fashion.

Preferably, the membrane 45 is substantially elliptical and more preferably either the upper portion 55 or the lower portion 60 of the membrane 45 is tapered in width to correspond to the palate 80 for proper and easier placement thereon. In the embodiment of the dental dam 40 shown in the drawings, the upper portion 55 is so tapered and helps maintain the upper portion 55 on the central portion of the palate 80 without sliding down the gums towards the upper teeth. The tapered or narrower upper portion 55 rests comfortably on the palate 80 regardless of its shape. The membrane 45 can be from about 8 cm to about 13 cm long, and from about 4 cm to about 8 cm wide. Preferably, the lower portion 60 of the membrane 45 is from about 4 cm to about 8 cm wide, the middle portion 65 of the membrane 45 can be from about 3 cm to about 7 cm wide, and the upper portion 55 of the membrane is 45 from about 1.5 cm to about 3 cm wide. Other shapes and sizes for the membrane 45 are also possible and are contemplated by the present invention.

The frame 50 comprises a spring-like member normally assuming a form with minimum potential energy stored in the spring-like member such as a planar form shown in FIG. 3 for example. The dental dam 40 can be folded along the middle portion 65 of the membrane 45 and inserted into the mouth as shown in FIGS. 2 and 8. The spring restoring action of the frame 50 urges the upper portion 55 of the dental dam against at least a portion of the palate 80 and the lower portion 60 against at least a portion of the tongue 85, such that the middle portion 65 substantially blocks the oral cavity 70 in the mouth of the user. So positioned, at least portions of the frame 50 are proximate the inner portion 90 of the user's teeth 95. The membrane 45 need not be punctured as it does not cover the portion of the teeth which need remain exposed for the dental procedure. No clamps are necessary to hold the dental dam 40 in place, no anesthesia is required for installing the dental dam 40, the dental dam 40 does not cover the lips or the face and no external frame or strap is necessary.

Figure 4:
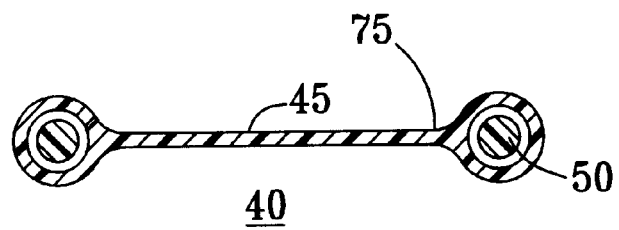
FIG. 4 is a cross-sectional view of the intraoral dental dam taken along the II—II line of FIG. 3.

In the embodiment of the dental dam 40 described herein, the frame 50 comprises a closed loop member to which the entire perimeter 75 of the membrane 45 is attached. The frame 50 can be shaped and sized to hold the membrane 45 taut to restrain the frame 50. The frame 50 can also be shaped and sized to correspond to the perimeter 75 of the membrane 45. The resilient member can be made from any spring like material including flexible tube, springs, or rigid rubber. Referring to FIG. 4, the frame 50 is cylindrical in cross-section, but other shapes are also possible and contemplated by the present invention. The resilient member can also be of the same material as the membrane 45. The resilient member can be from about 3 mm to about 5 mm thick. The frame 50 can be selected such that the restoring action of the frame 50 helps maintain the mouth in an open position when the dental dam 40 disposed in the mouth in an intraoral fashion.

Figure 5:
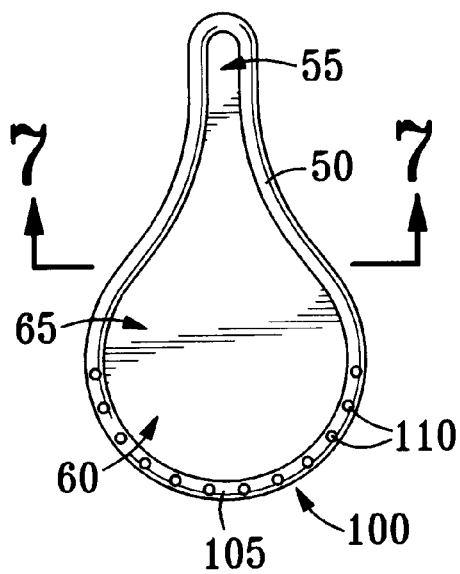
FIG. 5 is a plan view of the underside of an embodiment of an intraoral dental dam having suction openings along its perimeter according to another aspect of the present invention.
Figure 6:
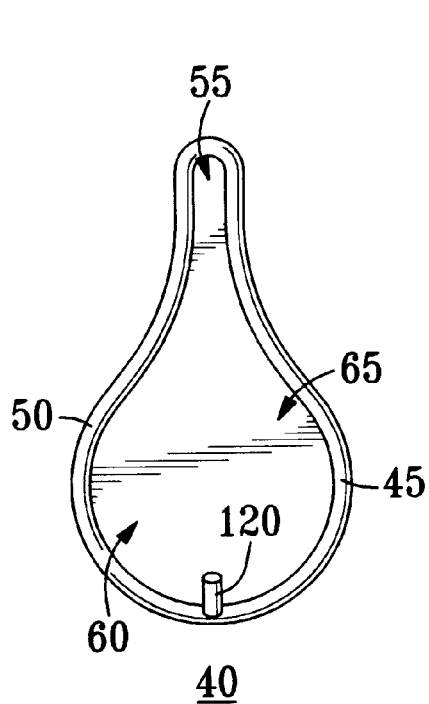
FIG. 6 is a plan view of the upper side of the dental dam of FIG. 5 showing an outlet opening.

Referring to FIGS. 5 and 6, the dental dam 40 can further comprise suction means 100 along at least a portion the frame 50 for removing fluids from the mouth. The suction means 100 can comprise at least one suction tube 105 having inlet openings 110 along its walls for removing fluids from the mouth into the tube 105. The suction tube 105 can further include at least one outlet opening 120 for removing fluids from the tube 105 via a central suction unit.

Figure 7:
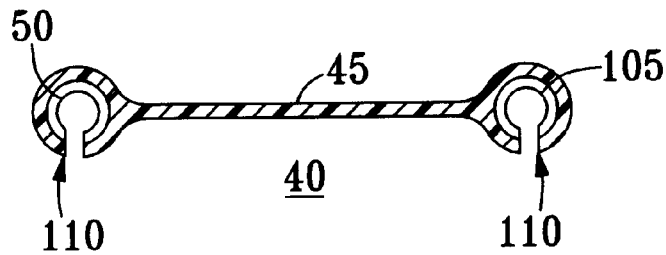
FIG. 7 is a cross-sectional view of the intraoral dental dam taken along the III—III line of FIG. 5.

Referring to FIG. 7, alternatively, at least a portion of the frame 50 can comprise a tube 105 having inlet openings 110 along its walls for removing fluids from the mouth into the tube 105, and at least one outlet opening 120 for removing fluids from the tube 105. The inlet openings 110 can be positioned on the tube 105 to most effectively remove fluids collecting in the mouth. FIG. 5 is a plan view of the underside of the dental dam 40 having suction openings 110, wherein the underside of the dental dam 40 corresponds to the tongue 85. As shown in FIG. 5, preferably, the inlet openings 110 are positioned on the frame 50 along the lower portion 60 of the membrane 45 adjacent the gums of the front teeth. The inlet openings 110 can also be positioned on other locations on the frame 50 as desired. Each inlet opening 110 can be from about 1 mm to about 2 mm in diameter, and the frame 50 can include from about 5 to about 20 inlet openings 110 therein. FIG. 6 is a plan view of the upper side of the dental dam of FIG. 5 showing the outlet opening 120.

The intraoral dental dam 40 of the present invention solves the problems of existing dental dams and provides several advantages including: the membrane 45 need not be punctured to isolate teeth; the dental dam 40 does not need clamps or extra-oral frames; the dental dam 40 can be installed and removed quickly and easily in a matter of seconds as compared to about half an hour for existing dental dams; the dental dam 40 covers the oral cavity 70 at the end of the mouth to protect the patient from swallowing debris or dental items; the dental dam 40 rests against the gums from the inside so that it does not interfere with the teeth; the dental dam 40 does not require anesthesia for installation, and enables the patient to close her mouth completely when, for example, trying the fit of multiple crowns and when there is a need to check the bite; the dental dam 40 can be used for any dental procedure and is flexible and non-irritating to the patient. Further, the suctions means 100 along the frame 40 can remove fluids such as saliva which pools under the tongue 85, thus creating a clean and dry environment to help maximize the physical properties of many dental materials which are easily distorted when they come in contact with moisture.

Because the dental dam 40 of the present invention is simple to use and does not interfere with the teeth or closure of the mouth, it can be used in various fields of dentistry for multiple procedures. For example, in Prosthodontics where the dentist needs to place several crowns in the mouth at the same time, without cementing them, the crowns may dislodge and fall into the patient's mouth. If the patient is in a supine position, the patient can readily inhale the crowns through the oral cavity at the end of the mouth, and if any of the crowns enter the lungs, they can cause severe injury. Further, because the dental dam 40 of the present invention is simple to use, it saves time and labor, and encourages regular use by the dentists. Further, the dental dam 40 as installed, provides a dry environment around the target teeth for dental materials such as fillings to achieve their best physical properties. The suction means 100 also helps keep target tooth and the proximate area dry by evacuating fluids from underneath the tongue 85.

The dental dam 40 of the present invention is specially useful in Pedodontics where the patients are typically young children. Children can be difficult to manage in a dental chair and are easily irritated by the conventional rubber dental dams 10 which not only hurt them but also cover half of their faces. The dental dam 40 of the present invention solves such problems as it can be quickly and easily placed in the young patient's mouth without any pain or discomfort. The dental dam 40 helps keep the operative site dry and the tongue out of the way.

The dental dam can be manufactured by an injection molding process. Such process can, for example, include the steps of: (1) molding wax or other substance into the shape of the membrane 45 based on desired measurements for the membrane 45, (2) creating an injection cavity in the mold, (3) injecting the material of choice for the membrane 45 into the mold cavity, (4) after a cool off period, opening the mold and removing the membrane 45. The membrane is then wrapped around the spring-like frame 50 and secured using adhesives. Alternatively, the mold can be shaped and sized for the entire dental dam 40, and the spring-like frame 50 can be placed in the mold before step (3) above. In that case, for the embodiment of the dental dam 40 including the inlet openings 110 for removing fluids the mouth, the spring-like frame 50 can be a tube with openings in the walls, and the mold is shaped such that the injection material for the membrane 45 does not block the tube openings.

Other methods of manufacturing the dental dam 40 are also possible. For example, the membrane 45 and the frame 50 can be made on a computer-generated shaped mold. The mold has a flat surface with peripheral edges, the flat surface corresponding to the shape and size of a desired membrane. The mold can be dipped into a solution of desired material to form a thin layer thereon on said surface for the membrane 45 and then removed. The dipped mold can then be dried in heat and the thin layer removed from said surface. The periphery of the membrane 45 is then wrapped on a spring-like frame 50 and secured thereto using adhesives.

Although the present invention has been described in considerable detail with regard to the preferred versions thereof, other versions are possible. Therefore, the appended claims should not be limited to the descriptions of the preferred versions contained herein.

What is claimed is:

1. A intraoral dental dam comprising:
    (a) an elastic membrane having:
        (i) an upper portion,
        (ii) a lower portion;
        (iii) a middle portion corresponding to the top cavity in the user's mouth, the middle portion extending between the upper and lower portions; and
        (iv) a perimeter; and
    (b) means for fitting said dam in the user's mouth proximate the inner portion of the user's teeth, said means comprising a resilient frame, at least a portion of the perimeter of the membrane being attached to at least a portion of the frame to form an integral dental dam, wherein the frame includes a perimeter sized to fit in a user's mouth proximate the inner portion of the user's teeth, such that when the dental dam is disposed in the user's mouth the upper portion rests against a least a portion of the palate, the lower portion rests over a least a portion of the tongue, the middle portion substantially blocks the oral cavity, and at least portions of the frame are proximate the inner portion of the user's teeth, leaving said teeth substantially exposed.

2. The dental dam of claim 1, wherein the frame comprises a spring-like member wherein the dental dam can be folded along the middle portion of the membrane and inserted into the mouth, such that a restoring action of the frame reopens the dental dam to a partially folded position with the upper portion of the dental dam resting against at least a portion of the palate, the lower portion resting over at least a portion of the tongue, the middle portion blocking the oral cavity, and at least portions of the frame being proximate the inner portion of the user's teeth, leaving said teeth substantially exposed.

3. The dental dam of claim 2, wherein the frame comprises a closed loop spring-like member.

4. The dental dam of claim 1, wherein the frame comprises a spring-like member and wherein the membrane is held taut by the frame to restrain the frame.

5. The dental dam of claim 4 wherein the dental dam can be folded along the middle portion of the membrane and inserted into the mouth, such that a restoring action of the frame reopens the dental dam to a partially folded position with the upper portion of the dental dam resting against at least a portion of the palate, the lower portion resting over at least a portion of the tongue, the middle portion blocking the oral cavity, and at least portions of the frame being proximate the inner portion of the user's teeth, leaving said teeth substantially exposed.

6. The dental dam of claim 1, further comprising suction means along at least a portion of the frame for removing fluids from the mouth.

7. The dental dam of claim 6, wherein the suction means comprises at least one suction tube having inlet openings along its walls for removing fluids from the mouth.

8. The dental dam of claim 7, wherein the at least one suction tube further includes at least one outlet opening for removing fluids from the tube.

9. The dental dam of claim 1, wherein at least a portion of the frame comprises a tube having inlet openings along its walls for removing fluids from the mouth.

10. The dental dam of clam 9, wherein the tube includes at least one outlet opening for removing fluids from the tube.

11. The dental dam of claim 1, wherein the frame is shaped and sized to correspond substantially to the perimeter of the elastic membrane.

12. An intraoral dental dam comprising:
    (a) an elastic membrane having:
        (i) an upper portion;
        (ii) a lower portion;
        (iii) a middle portion corresponding to the oral cavity in the user's mouth, the middle portion extending between the upper and lower portions; and
        (iv) a perimeter; and
    (b) means for fitting said dam in the user's mouth proximate the inner portion of the user's teeth, said means comprising a frame comprising a closed loop spring-like member, the perimeter of the membrane being attached to at least a portion of the frame to form an integral dental dam such that the membrane is held taut by the frame, restraining the frame;

wherein the dental dam can be folded along the middle portion of the membrane and inserted into the mouth, such that a restoring action of the frame reopens the dental dam to a partially folded position so that the upper portion rests against at least a portion of the palate, the lower portion rests over a least a portion of the tongue, the middle portion substantially blocks the oral cavity, and at least portions of the frame are substantially adjacent the inner portion of the user's teeth, leaving said teeth substantially exposed.

13. The dental dam of claim 12, further comprising a suction means along at least a portion of the frame for removing fluids from the mouth.

14. The dental dam of claim 13, wherein the suction means comprises at least one suction tube having inlet openings along its walls for removing fluids from the mouth.

15. The dental dam of claim 14, wherein the at least one suction tube further includes at least one outlet opening for removing fluids from the tube.

16. The dental dam of claim 12, wherein at least a portion of the frame comprises a tube having inlet openings along its walls for removing fluids from the mouth.

17. The dental dam of claim 16, wherein the tube includes at least one outlet opening for removing fluids from the tube.

18. The dental dam of claim 12, wherein the frame is shaped and sized to correspond substantially to the perimeter of the elastic membrane.

19. An intraoral dental dam comprising:
(a) an elastic membrane having:
   (i) an upper portion;
   (ii) a lower portion;
   (iii) a middle portion corresponding to the oral cavity in the user's mouth, the middle portion extending between the upper and lower portions; and
   (iv) a perimeter; and
(b) means for fitting said dam in the user's mouth proximate the inner portion of the user's teeth, said means comprising a spring-like frame comprising a tubular member along at least a portion of the frame, the perimeter of the membrane being attached to the frame to form an integral dental dam such that the membrane is held taut by the frame, at least a portion of the walls of the tubular member having openings therethrough for removing fluids from the mouth into the tube and at least one outlet for removing fluids from the tube;

wherein the dental dam can be folded along the middle portion of the membrane and inserted into the mouth, such that a restoring action of the frame reopens the dental dam to a partially folded position so that the upper portion rests against at least a portion of the palate, the lower portion rests over at least a portion of the tongue, the middle portion substantially blocks the oral cavity, and at least portions of the frame are adjacent the inner portion of the user's teeth, leaving said teeth substantially exposed.

20. The dental dam of claim 19, wherein the lower portion of the membrane tapers into the upper portion of the membrane.

* * * * *